US008287476B2

(12) United States Patent
Bettiol

(10) Patent No.: US 8,287,476 B2
(45) Date of Patent: Oct. 16, 2012

(54) PROTECTIVE DEVICE FOR A JOINT, PARTICULARLY FOR A KNEE

(75) Inventor: Silvano Bettiol, Volpago Del Montello (IT)

(73) Assignee: Tryonic Limited, London (GB)

( * ) Notice: Subject to any disclaimer, the term of this patent is extended or adjusted under 35 U.S.C. 154(b) by 291 days.

(21) Appl. No.: 12/735,464

(22) PCT Filed: Jan. 23, 2009

(86) PCT No.: PCT/EP2009/050784
§ 371 (c)(1),
(2), (4) Date: Jul. 19, 2010

(87) PCT Pub. No.: WO2009/092798
PCT Pub. Date: Jul. 30, 2009

(65) Prior Publication Data
US 2010/0286579 A1    Nov. 11, 2010

(30) Foreign Application Priority Data

Jan. 25, 2008    (IT) .............................. VE2008A0005

(51) Int. Cl.
*A61F 5/00*    (2006.01)
(52) U.S. Cl. .......................................... 602/16; 602/26
(58) Field of Classification Search .................... 602/16, 602/20–27; 128/877–879, 882; 2/22
See application file for complete search history.

(56) References Cited

U.S. PATENT DOCUMENTS

| 4,136,404 A | * | 1/1979 | Lange | ................................. 2/22 |
| 5,741,221 A | | 4/1998 | Wetz | |
| 2007/0010772 A1 | | 1/2007 | Ryan | |

FOREIGN PATENT DOCUMENTS

| DE | 24 32 766 A1 | 3/1975 |
| WO | WO 03065942 A | 8/2003 |

* cited by examiner

*Primary Examiner* — Michael A. Brown
(74) *Attorney, Agent, or Firm* — Modiano & Associati; Daniel O'Byrne

(57) ABSTRACT

A protective device for a joint, particularly for a knee, comprising a first frame to which a second frame is articulated by means of a pair of hinges that during use are arranged proximate to the two sides of the joint, the hinges being constituted by a first base and a second base, which are associated respectively with the first and second frames and are rotatably connected to each other by means of a first arm and a second arm, which are mutually crossed. The ends of the first arm are rotatably associated with the first and second bases, both by means of substantially hemispherical mutual engagement surfaces; one end of the second arm is associated rotatably with the first base by means of a substantially hemispherical mutual engagement surface and the other end of the second arm is associated with the second base by means of a substantially flat mutual engagement surface.

28 Claims, 7 Drawing Sheets

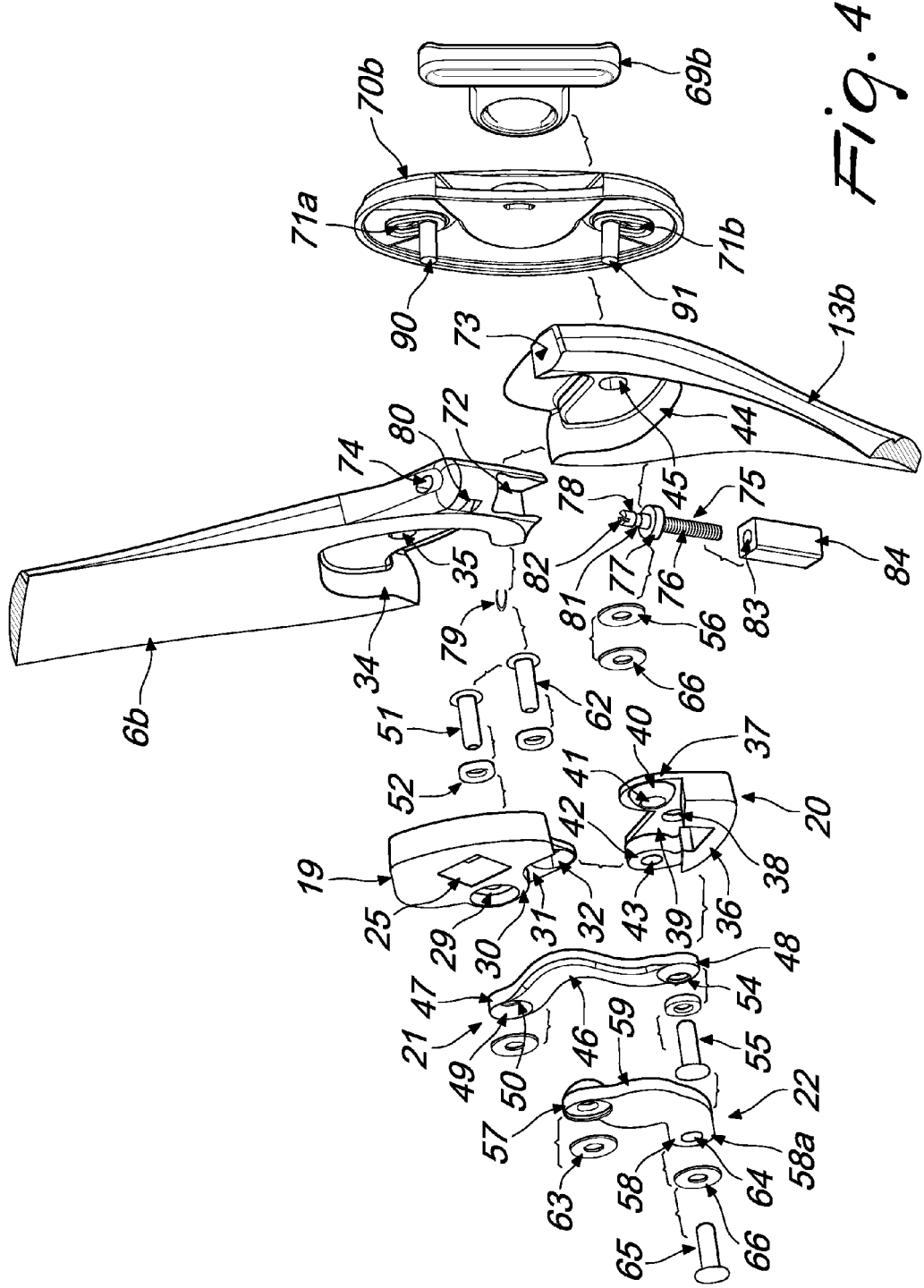

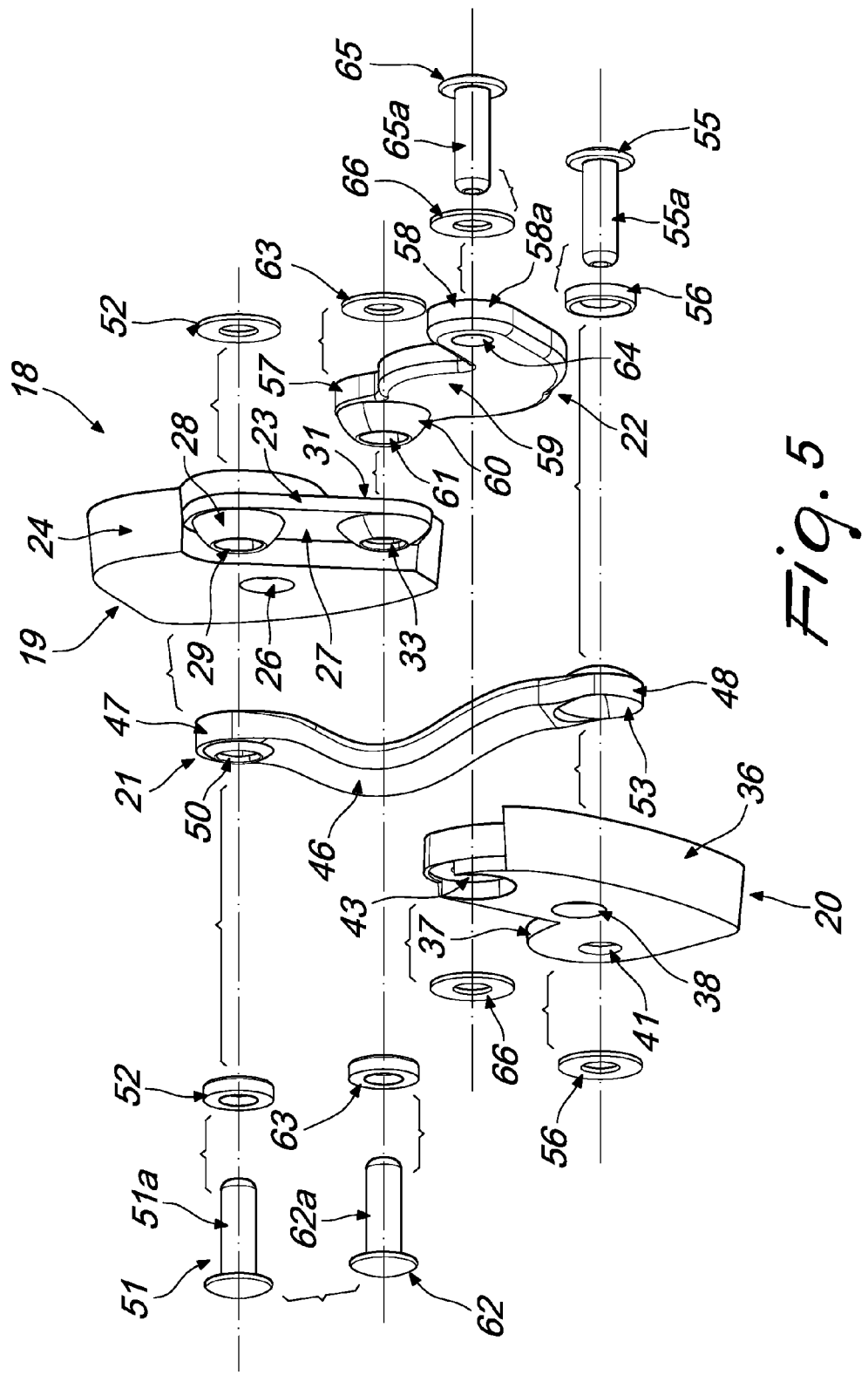

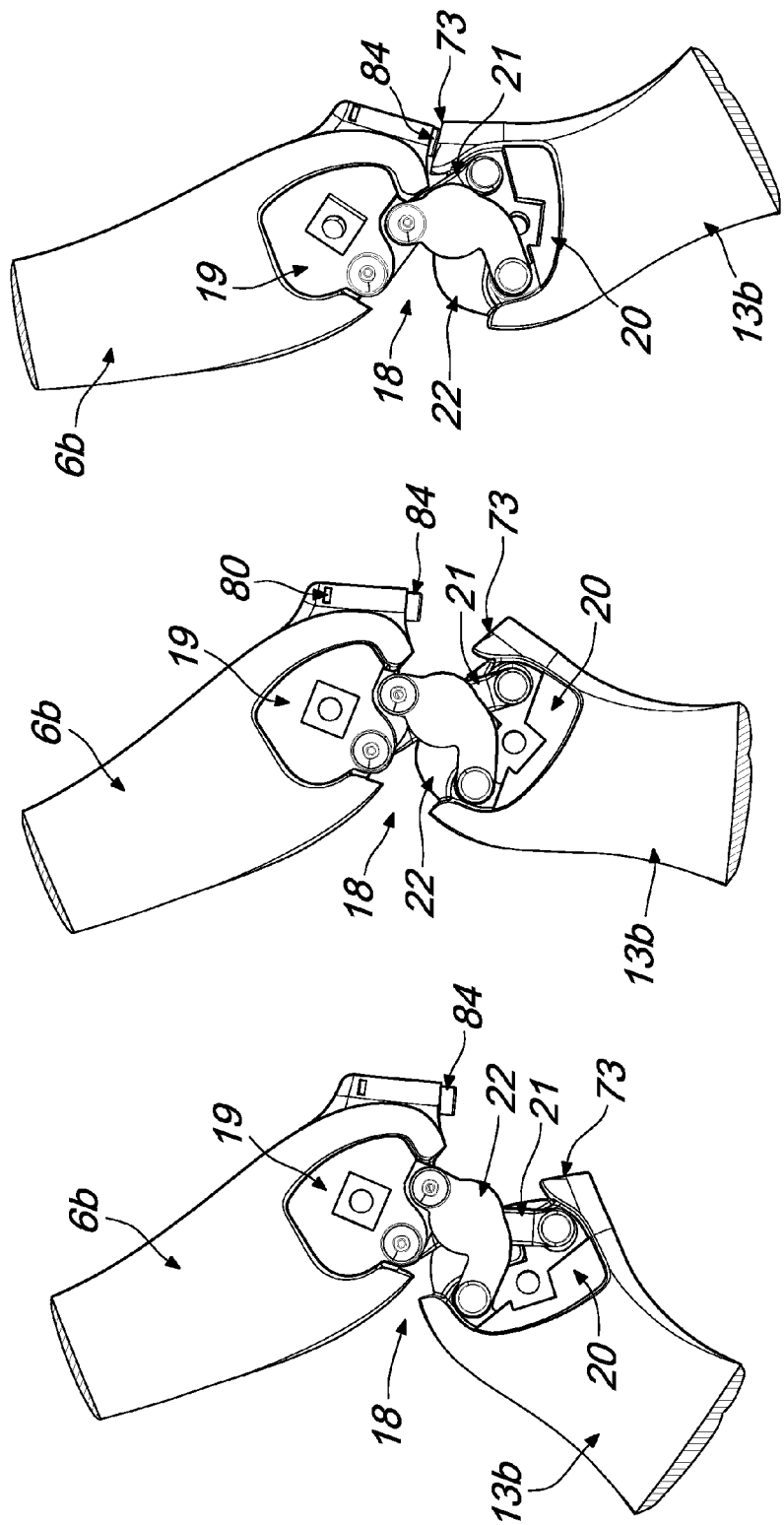

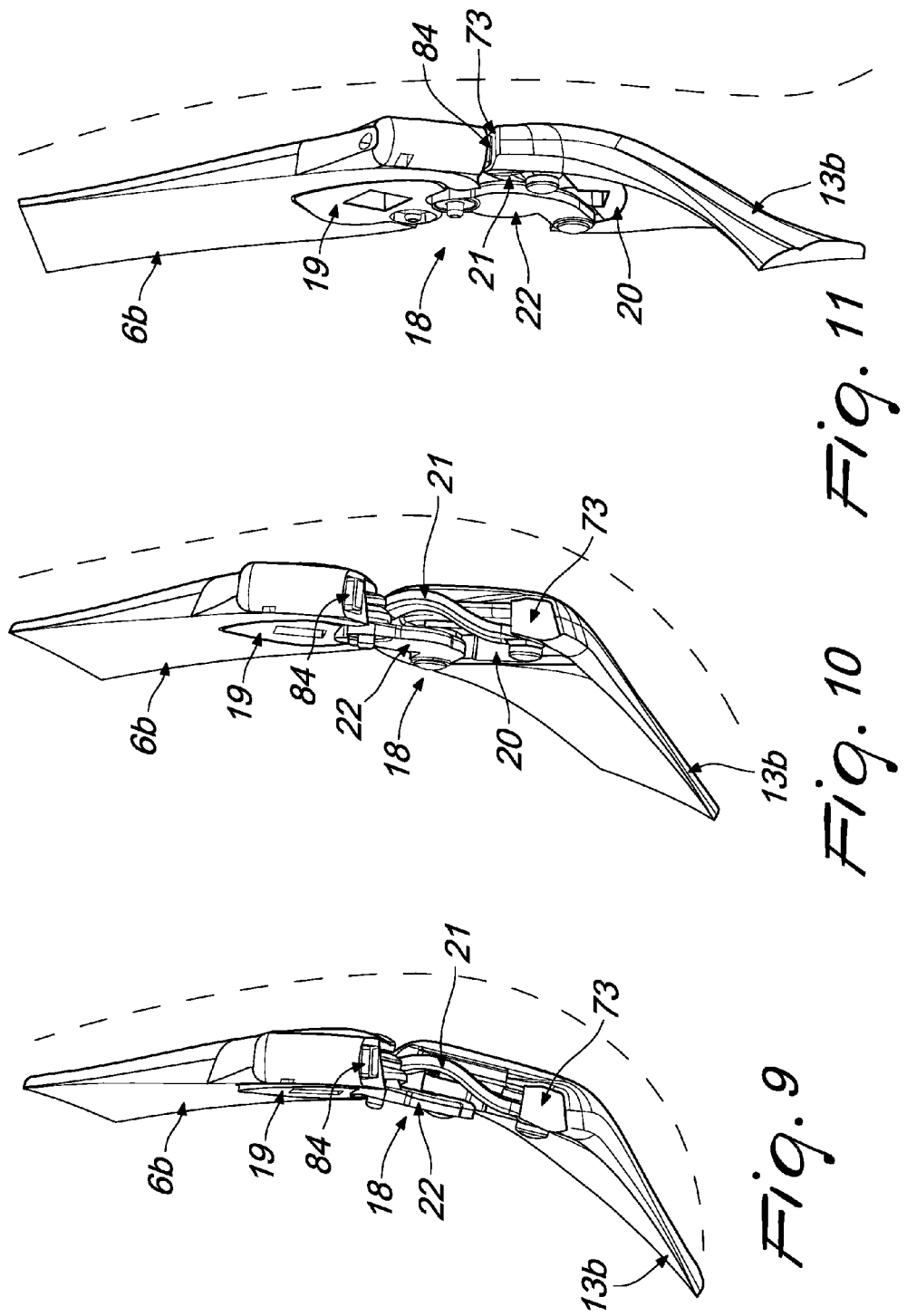

PROTECTIVE DEVICE FOR A JOINT, PARTICULARLY FOR A KNEE

The present invention relates to a protective device for a joint, particularly for a knee.

BACKGROUND OF THE INVENTION

Currently, in order to offer support to the knee joint, particularly during rehabilitation following traumas, lesions or surgical procedures, and/or during the practice of sports that are particularly onerous for joints, such as for example motocross, knee pads are used which are constituted by two frames that can be fixed respectively to the thigh and to the tibia and are mutually articulated by means of two appropriately provided hinges that during use are arranged proximate to the two sides of the knee.

The hinges guide the movement of the knee during the bending and extension of the leg, preventing such knee from performing abnormal movements that might harm it.

U.S. Pat. No. 4,886,054 is known, for example, which discloses a protective device for the knee, which is constituted by a first frame and a second frame, which are mutually articulated by means of two hinges constituted by a first flat base to the upper surface of which a second likewise flat base is fixed, its perimetric edge forming a cam arranged so as to cover at least partially the upper surface of the first base.

The hinges comprise a first arm and a second arm, which are pivoted to the outer surface of the second base, and a guiding block, which is fixed to the first base and has at least one guide that is provided with a first limit stop and with a second limit stop and is arranged so as to face the cam formed by the perimetric edge of the second base.

The hinges further comprise at least one stop lever, which has an elongated shape and is provided with a first end, which is pivoted to the first arm or to the second arm, and with a second end, which is slidingly associated within the guide formed in the guiding block; such stop lever is arranged proximate to the cam formed by the second base, so that during the rotation of the first or second arm to which such stop lever is connected, a portion thereof slides on the cam, pushing the second end of such stop lever within the guide.

The hinge further comprises a linkage, which connects the first arm and the second arm, so that the rotation of one of such arms causes the rotation of the other arm.

The rotation angle between the first arm and the second arm is limited by the abutment of the second end of the stop lever against the limit stops provided at the first and second ends of the guide.

This known type of solution, however, has a drawback: the first and second arms of the hinges in fact always move along two planes that are substantially parallel and constantly equidistant with respect to each other and therefore do not follow the actual motion of the knee, which is more complex in the various flexing conditions; accordingly, this can compromise both the support of the joint and the user comfort.

Further, these known types of hinge are structurally complex and therefore have a high cost.

Moreover, the stopping of the rotation of the hinges in both directions of rotation can be sudden, since it is achieved by means of the abutment of the second end of the stop lever arm against the limit stops provided in the guide, and this can compromise user comfort and safety.

WO03/065942 is also known which discloses a knee pad that comprises an upper frame and a lower frame, which are mutually connected by means of two hinges and are associated respectively with an upper sleeve and a lower sleeve, which can be arranged so as to wrap around the thigh and the calf of the user, and can be coupled thereto by way of two fastening elements provided with laces; such fastening elements are associated detachably with the respective frames by means of snap-acting buckles that allow, once the desired level of fastening has been set by means of the laces, to remove or put on the knee pad without losing the preset level of fastening.

Each hinge comprises an upper block and a lower block, which can be accommodated respectively in two complementarily shaped openings formed respectively in the upper frame and in the lower frame and can be locked in such openings by means of appropriately provided covers.

Two through openings are provided in the upper block and in the lower block and their lateral surface is shaped approximately like a spherical dome.

A front arm is arranged between one of the two openings of the upper block and one of the two openings of the lower block, and two hemispherical elements are associated with the ends of such front arm, are substantially shaped complementarily with respect to such openings and can be accommodated rotatably therein; a rear arm is arranged between the other two openings of the upper block and of the lower block, and two additional hemispherical elements are associated respectively with the ends of such rear arm, are substantially shaped complementarily with respect to such openings and can be accommodated rotatably in them.

The engagement between the hemispherical elements and the lateral surface of the respective openings allows the upper block and the lower block to perform mutual movements both parallel to the axis of the leg and in a radial direction with respect to such leg.

The hinges of such known type of knee pad further comprise a cable, in which a first end is fixed in an opening provided proximate to the end of the rear arm that is associated with the upper block and a second end is arranged in a channel formed in such upper block; the degree of protrusion of the cable from the channel can be adjusted by means of an appropriately provided adjustment screw.

The presence of the cable limits the rotation of the rear arm with respect to the upper block, and therefore of the upper frame with respect to the lower block, in the direction of extension of the leg; further, the cable has a slight elasticity, which creates a damping effect in the step for blocking the mutual rotation of the two frames in the direction of the extension of the leg, thus reducing the risks of possible traumas for the knee.

Even this known type of solution, however, has a drawback; it is in fact structurally complicated and requires a long time for its construction, and this entails a very high cost for it.

Further, the cable adapted to limit the mutual rotation of the upper frame and of the lower frame in the direction of the extension of the leg can be subject to frequent breakage, particularly due to the wear caused by its friction against the rigid components of the knee pad.

This known type of solution further has another drawback; due to the particular shape of the hinges, the upper frame and the lower frame can in fact be made to perform a translational motion with respect to each other, in the condition of maximum extension of the leg, in the direction defined by an axis that passes through the two hinges; this known type of knee pad, therefore, in the condition in which the leg is extended, is not able to protect the knee effectively against any stresses that tend to produce the lateral translational motion of the tibia with respect to the thigh.

SUMMARY OF THE INVENTION

The aim of the present invention is to solve the above-mentioned drawbacks, by providing a device that allows to protect effectively a joint, particularly the knee joint, while ensuring high comfort to the user.

Within this aim, an object of the invention is to provide a device which ensures effective protection to a joint, particularly the knee joint, allowing it to perform the desired movements easily.

Another object of the invention is to provide a device which is solid and durable.

Another object of the invention is to provide a device that is structurally simple and has low manufacturing costs.

This aim and these and other objects, which will become better apparent hereinafter, are achieved by a protective device for a joint, particularly for a knee, comprising a first frame to which a second frame is articulated by means of a pair of hinges that during use are arranged proximate to the two sides of said joint, said hinges being constituted by a first base and a second base, which are associated respectively with said first and second frames and are rotatably connected to each other by means of a first arm and a second arm, characterized in that said first arm and said second arm are mutually crossed, the ends of said first arm being rotatably associated with said first and second bases, both by means of substantially hemispherical mutual engagement surfaces, one end of said second arm being associated rotatably with said first base by means of a substantially hemispherical mutual engagement surface, the other end of said second arm being associated with said second base by means of a substantially flat mutual engagement surface.

BRIEF DESCRIPTION OF THE DRAWINGS

Further characteristics and advantages of the invention will become better apparent from the following detailed description of a particular but not exclusive embodiment thereof, illustrated by way of non-limiting example in the accompanying drawings, wherein:

FIG. 4 is an exploded perspective view of some details of the device according to the invention;

FIG. 5 is an exploded perspective view of some details of the device according to the invention;

FIGS. 6, 7 and 8 are side views of a hinge of the device according to the invention in various operating positions;

FIGS. 9, 10 and 11 are front perspective views of a hinge of the device according to the invention in various operating positions.

DESCRIPTION OF THE PREFERRED EMBODIMENTS

Figure 1:
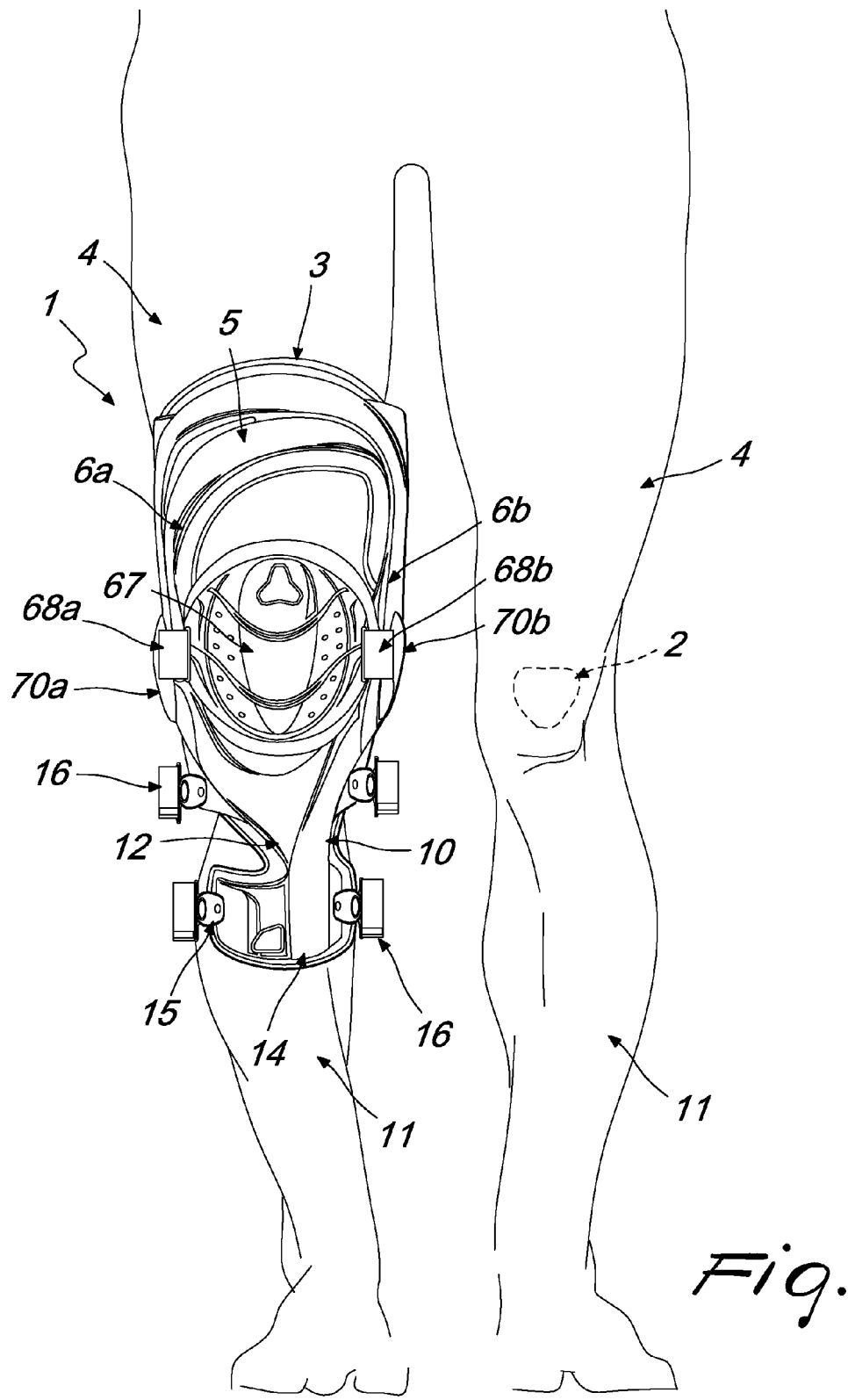
FIG. 1 is a schematic front view of a protective device according to the invention applied to a leg.
Figure 2:
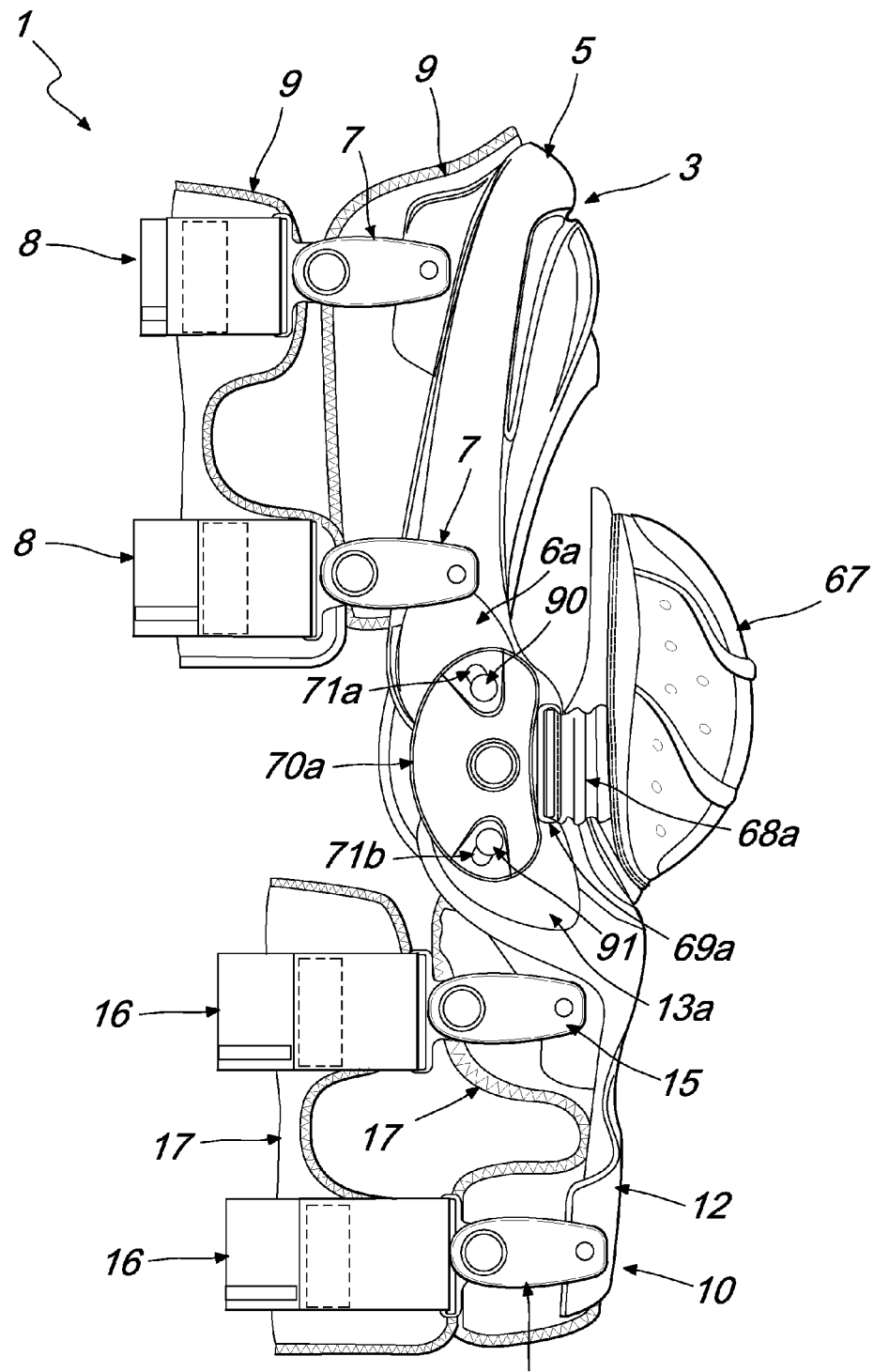
FIG. 2 is a side view of the device according to the invention.
Figure 3:
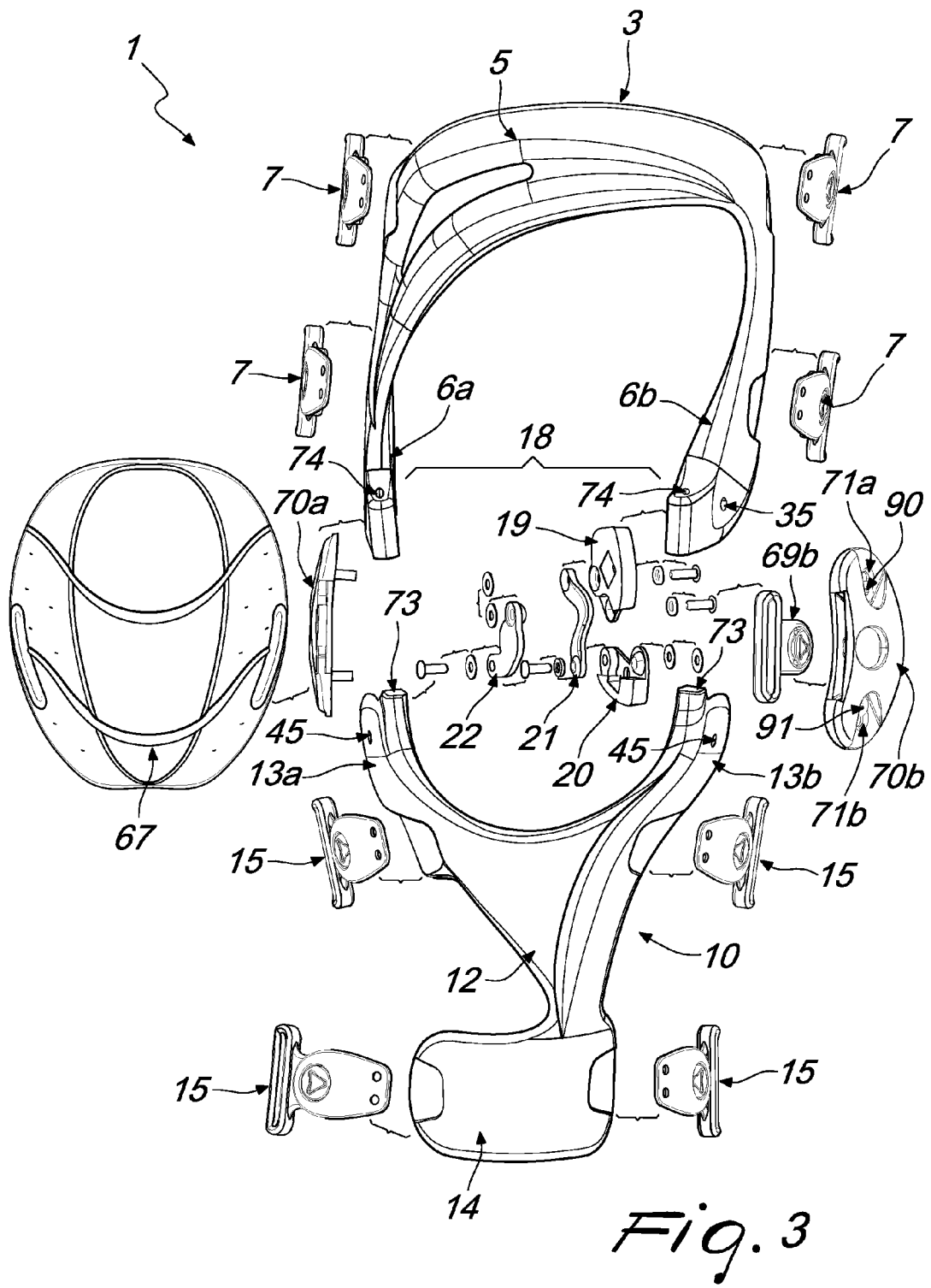
FIG. 3 is an exploded perspective view of some components of the device according to the invention.

In the exemplary embodiments that follow, individual characteristics, given in relation to specific examples, may actually be interchanged with other different characteristics that exist in other exemplary embodiments.

Moreover, it is noted that anything found to be already known during the patenting process is understood not to be claimed and to be the subject of a disclaimer.

With reference to the figures, the reference numeral 1 generally designates a protective device for a joint, particularly for a knee 2.

Hereinafter, the device 1 will be described with reference to its application to the knee 2; the device 1 can be used in any case also to protect other joints, such as for example an elbow.

The device 1 comprises a first frame 3, which can be associated preferably with a thigh 4 of the user and is shaped, in the embodiment shown in the accompanying figures, approximately like an inverted letter U, so as to define a base 5, which has an arc-like profile in plan view, that can be arranged so as to cover the front region and part of the lateral regions of the thigh 4.

Two first wings 6a and 6b protrude toward the knee 2 from the base 5 and can be positioned, during use, adjacent to the lateral regions of the thigh 4, with their free ends arranged proximate to the two sides of the knee 2.

First means for detachable fixing to the thigh 4 are associated with the first frame 3 and advantageously comprise first snap-acting buckles 7, which are fixed laterally to the first frame 3 and support first straps 8 that during use wrap around the rear region of the thigh 4, so as to keep the first frame 3 rigidly coupled to such thigh; first means for adjusting their degree of fastening, not shown in the accompanying figures, can be associated with the first straps 8.

Advantageously, one or more first layers 9 made of soft material are associated with the internal surface of the first frame 3 and optionally also of the first straps 8 and are adapted to increase user comfort.

A second frame 10 is articulated to the first frame 3, can be associated with a tibia 11 of the user during use, and is shaped, in the embodiment shown in the accompanying figures, approximately like a letter Y, so as to form an approximately vertical portion 12 that has, in plan view, an arc-like profile, which can be arranged so as to cover partially the front region of the tibia 11.

Two second wings 13a and 13b protrude from the approximately vertical portion 12 in the direction of the knee 2 and can be positioned, during use, adjacent to the lateral regions of the tibia 11, with their free ends arranged proximate to the two sides of the knee 2.

Advantageously, a tab 14 is associated with the end of the approximately vertical portion 12 that lies opposite the second wings 13a and 13b and has, in plan view, an arc-like shape that during use wraps around part of the front region and of the lateral regions of the tibia 11.

Second means for removable fixing to the tibia 11 are associated with the second frame 10 and comprise advantageously second snap-acting buckles 15, which are fixed laterally to the second frame 10 and support second straps 16 that during use wrap around the rear region of the tibia 11, so as to keep the second frame 10 jointly connected to such tibia; it is possible to associate with the second straps 16 second means for adjusting their degree of fastening, not shown in the accompanying figures.

Advantageously, one or more second layers 17 made of soft material and adapted to increase user comfort are associated with the internal surface of the second frame 10 and optionally also of the second straps 16.

The first frame 3 and the second frame 10 are mutually articulated by means of a pair of hinges 18, each of which comprises advantageously a first base 19, which is associated with the first frame 3, and a second base 20, which is associated with the second frame 10, and can be mutually connected rotatably by means of a first arm 21 and a second arm 22 arranged so as to cross each other and described hereinafter.

Advantageously but not necessarily, the first base 19 has a footing 23, which has an approximately rectangular plan shape, and a contiguous first head 24, which has a teardrop shape in plan view.

A first cavity 25 is provided approximately centrally to the first head 24, and a first hole 26 for engagement with the first frame 3 is provided on its bottom.

Advantageously, a first spherical dome 28 protrudes from a first surface 27 of the footing 23 that during use is directed away from the knee 2, and a second through hole 29 is provided axially with respect to such dome.

In a second surface 30 of the footing 23 that during use is directed toward the knee 2 there is conveniently a first recess 31, at which there is a first substantially hemispherical seat 32, axially to which a third through hole 33 is provided.

The first base 19 can be associated with one first wing 6a or 6b of the first frame 3, arranging it in a complementarily shaped second seat 34, which is formed at one end of the first wing 6a or 6b, on the bottom of which a fourth hole 35 is provided at the first hole 26 of the first head 24; the first base 19 can be fixed in the second seat 34 for example by means of an appropriately provided first screw 90, optionally with the interposition of an appropriately provided plate 70a, 70b, which will be described hereinafter.

Advantageously, the second base 20 has an approximately L-shaped plan configuration, so as to define a first branch 36 and a second branch 37, which are approximately perpendicular to each other.

Approximately centrally with respect to the first branch 36 there is conveniently a fifth through hole 38 for engagement with the second frame 10.

A second spherical dome 40 protrudes at the second branch 37 from a third surface 39 of the second base 20 that during use is directed toward the knee 2, and a sixth through hole 41 is provided axially to such second dome.

A substantially flat resting abutment 42 is formed on the third surface 39 of the second base 20, at the first branch 36, and a seventh through hole 43 is provided approximately centrally to such abutment.

The second base 20 can be associated with one second wing 13a or 13b of the second frame 10, arranging it in a complementarily shaped third seat 44 that is formed at one end of the second wing 13a or 13b, on the bottom of which an eighth hole 45 is provided at the fifth hole 38 of the second base 20.

The second base 20 can be fixed in the third seat 44 for example by means of an appropriately provided second screw 91, which is associated with the fifth hole 38 and with the eighth hole 45, optionally with the interposition of one appropriately provided plate 70a, 70b that will be described hereinafter.

Advantageously, the first arm 21 has a substantially rectangular plan shape and has a curved central portion 46, which during use is arranged so that its concave surface is directed toward the knee 2; conveniently, the first arm 21 has a first end and a second end, designated respectively by the reference numerals 47 and 48, which are substantially flat and approximately parallel to each other.

A fourth seat 49 is provided at the first end 47 of the first arm 21, in the surface thereof that during use is directed toward the knee 2, and is shaped substantially complementarily with respect to the first spherical dome 28 of the first base 19, axially to which a ninth hole 50 is provided.

The first end 47 of the first arm 21 can thus be associated rotatably with the first base 19, arranging the first spherical dome 28 in the fourth seat 49 and preferably coupling them by means of an appropriately provided first rivet 51, which is inserted in the second hole 29 and in the ninth hole 50, optionally with the interposition of appropriately provided first washers 52; the first rivet 51 has a first stem 51a that has a smaller diameter than the second hole 29 and the ninth hole 50, so as to allow the first spherical dome 28 to move in the three directions within the third seat 44.

Advantageously, a fifth seat 53 is provided at the second end 48 of the first arm 21, in the surface thereof that during use is directed away from the knee 2, and is shaped substantially complementarily with respect to the second spherical dome 40 of the second base 20, axially to which a tenth hole 54 is formed.

The second end 48 of the first arm 21 is associated rotatably with the second base 20 by arranging the second spherical dome 40 in the fifth seat 53 and coupling them for example by means of an appropriately provided second rivet 55, which is inserted in the sixth hole 41 and in the tenth hole 54, optionally with the interposition of appropriately provided second washers 56; the second rivet 55 has a second stem 55a whose diameter is smaller than the diameter of the sixth hole 41 and of the tenth hole 54, so as to allow the second spherical dome 40 to move in the three directions within the fifth seat 53.

Advantageously, the second arm 22 has an approximately L-shaped plan configuration, so as to form a third branch 57 and a fourth branch 58, which are approximately mutually perpendicular; advantageously, the third branch 57 is provided centrally with an increased width or expansion 59.

Advantageously, proximate to the free end of the third branch 57, in the surface thereof that during use is directed away from the knee 2, there is a third spherical dome 60, which is shaped substantially complementarily to the first seat 32 of the first base 19 and axially to which an eleventh hole 61 is provided.

The third branch 57 of the second arm 22 can thus be associated rotatably with the first base 19 by arranging the third spherical dome 60 in the first seat 32 of the first base 19 and by coupling the latter and the second arm 22 for example by means of an appropriately provided third rivet 62 inserted in the third hole 33 and in the eleventh hole 61, optionally with the interposition of appropriately provided third washers 63; the third rivet 62 has a third stem 62a, whose diameter is smaller than the diameter of the third hole 33 and of the eleventh hole 61, so as to allow the third spherical dome 60 to move in the three directions within the first seat 32.

Advantageously, proximate to a free end 58a of the fourth branch 58, the surface thereof that during use is directed away from the knee 2 is substantially flat and has a twelfth hole 64.

The fourth branch 58 of the second arm 22 can be associated rotatably with the second base 20 by arranging its free flat end 58a so that it engages the complementarily shaped resting abutment 42 of the second base 20 and by rotatably coupling the latter and the second arm 22 by means of an appropriately provided fourth rivet 65, which is inserted in the seventh hole 43 and in the twelfth hole 64, optionally with the interposition of appropriately provided fourth washers 66; the play between a fourth stem 65a of the fourth rivet 65, the seventh hole 43, and the twelfth hole 64 is reduced, so that the second arm 22 can rotate with respect to the second base 20 only by lying on a plane that is substantially parallel to the resting abutment 42.

The particular combination between the shape and the arrangement of the first and second arms and the shape of the surfaces for engagement between such arms and the first and second bases allow them to perform mutual rotary and translational motions that follow the movement of the knee.

Advantageously, the device 1 comprises means for front protection of the knee, which comprise for example a shell 67 made of rigid material, which is associated with the first frame 3 and with the second frame 10 by means of appropriately provided bands 68a, 68b, which are elastic and are fixed laterally to the shell 67 and to appropriately provided third snap-acting buckles 69a, 69b, which in turn are associated with two appropriately provided plates 70a, 70b, each of which is associated rotatably respectively with one first wing 6a, 6b and with one second wing 13a, 13b, proximate to the free ends thereof.

Advantageously, two slots 71a, 71b are provided in each of the plates 70a and 70b, and the first screw 90 and the second screw 91 are inserted respectively therein before they are inserted in the fourth hole 35 and in the eighth hole 45, in order to rotatably couple the plate 70a, 70b to the first and second frames 3, 10.

Advantageously, the device 1 comprises stroke limiting and shock-absorbing means, which comprise a second cavity 72, which has a polygonal and preferably approximately rectangular cross-section and is formed at the free end of the first wings 6a, 6b, in such a position that it faces, in the condition of maximum extension of the leg, shown for example in FIGS. 8 and 11, a stop abutment 73, which is provided at the free end of the second wings 13a, 13b.

As an alternative, in an embodiment that is not shown in the accompanying figures, the second cavity can be formed in the second wings 13a, 13b and the stop abutment 73 can be formed in the facing first wings 6a, 6b.

A first through opening 74 is provided conveniently in the bottom of the second cavity 72.

A third screw 75 is accommodated at least partially within the second cavity 72 and comprises a fifth threaded stem 76 and a second substantially cylindrical head 77, which during use is engaged with the bottom, not shown in the accompanying figures, of the second cavity 72.

A preferably cylindrical pivot 78 protrudes from the second head 77, on the opposite side with respect to the fifth stem 76, and during use is inserted in the first opening 74 and rotatably coupled therein by means of a stop ring 79, which is inserted in the first opening 74 through an appropriately provided second lateral opening 80 and is fixed to an annular slot 81 formed in the lateral surface of the pivot 78.

Advantageously, at the free end of the pivot 78 there are means adapted to allow to impart an axial rotation thereto, such as for example a slot 82 that can be engaged with the tip of a screwdriver.

The fifth stem 76 of the third screw 75 is screwed into a complementarily threaded third cavity 83, which is formed axially to a block 84, made of elastically deformable material, which in plan view is shaped substantially complementarily with respect to the second cavity 72, is partially inserted therein and protrudes from it with its free end; such end, during the mutual rotation of the first and second frames, abuts against the stop abutment 73, limiting this rotation in the direction of extension of the leg and simultaneously applying a shock-absorbing effect.

By imparting to the third screw 75 an axial rotation in the appropriate direction, it is possible to make the block 84 exit by a selected extent from the second cavity 72, thus allowing to adjust the maximum mutual rotation allowed between the first and second frames in the direction of extension of the leg.

The use of the device according to the invention is as follows.

With reference to the accompanying figures, the device 1 can be worn by arranging the first frame 3 so as to wrap around the thigh 4 at the front and the second frame 10 so as to wrap around the tibia 11 at the front, and by fixing such first and second frames respectively to the thigh 4 and to the tibia 11 by means of the first and second straps 8, 16.

During the movement of the leg, by way of the particular shape of the hinges 18, the first and second bases 19, 20, and therefore the first and second frames 3, 10 associated with them, perform mutual rotary and translational motions that follow the movement of the knee 2 also in its components in a direction that is diametrical with respect to the leg.

The condition of maximum extension allowed to the leg, shown in FIGS. 8 and 11, is achieved at the abutment of the blocks 84 against the respective stop abutments 73.

The elastically deformable material of which the blocks 84 are made has a shock-absorbing effect in reaching the condition of maximum extension of the leg, which reduces stresses on the articulation of the knee 2.

By way of the particular shape of the hinges 18, the first frame 3 and the second frame 10 are not allowed, in the condition of maximum extension of the leg, to perform mutual translational motions along an axis that passes through the hinges 18; the device 1 therefore protects effectively the articulation against stresses that tend to make the tibia perform a lateral translational motion with respect to the thigh, even in the condition in which the leg is extended.

It has thus been shown that the invention has achieved the proposed aim and objects, a protective device for a joint, particularly a knee, having been devised which is capable of protecting effectively such joint, ensuring high comfort to the user.

Further, the device according to the invention allows the joint to perform the desired movements easily.

Further, the device according to the invention is solid and durable.

Moreover, the presence of the blocks made of elastically deformable material allows to obtain a shock-absorbing effect in reaching the condition of maximum extension of the leg.

Further, the production costs of the device according to the invention remain low, since it is provided only by means of components that are easy to manufacture and/or assemble.

The invention is of course susceptible of numerous modifications and variations, all of which are within the scope of the appended claims.

Thus, for example, in an alternative embodiment, not shown in the accompanying figures, one of the two ends of the first arm might be associated rotatably with the first or second base by means of a substantially hemispherical mutual engagement surface, while the other end of such first arm might be associated respectively with the second base or with the first base by means of a substantially flat mutual engagement surface; in this case, the ends of the second arm would have to be associated rotatably with the first and second bases by means of the substantially hemispherical mutual engagement surfaces.

The materials used, as well as the dimensions that constitute the individual components of the invention, may of course be more pertinent according to specific requirements.

The various means for performing certain different functions need not certainly coexist only in the illustrated embodiment but can be present per se in many embodiments, including ones that are not illustrated.

The characteristics indicated as advantageous, convenient or the like may also be omitted or be replaced with equivalents.

The disclosures in Italian Patent Application No. VE2008A000005 from which this application claims priority are incorporated herein by reference.

What is claimed is:

1. A protective device for a joint, particularly for a knee, comprising a first frame to which a second frame is articulated by means of a pair of hinges that during use are arranged proximate to the two sides of said joint, said hinges being constituted by a first base and a second base, which are associated respectively with said first and second frames and are rotatably connected to each other by means of a first arm and a second arm, wherein said first arm and said second arm are mutually crossed, the ends of said first arm being rotatably associated with said first and second bases, both by means of substantially hemispherical mutual engagement surfaces, one end of said second arm being associated rotatably with said first base by means of a substantially hemispherical mutual engagement surface, the other end of said second arm being associated with said second base by means of a substantially flat mutual engagement surface.

2. The device according to claim 1, wherein on the surface of said first base that during use is directed away from said joint and on the surface of said second base that during use is directed toward said joint there are respectively a first spherical dome and a second spherical dome, above which the approximately complementarily shaped ends of said first arm are associated rotatably, on the surface of said first base that during use is directed toward said joint and on said surface of said second base that during use is directed toward said joint there being respectively a first seat shaped approximately like a spherical dome and a substantially flat resting abutment, with which the approximately complementarily shaped ends of said second arm are associated rotatably.

3. The device according to claim 2, wherein said first base is constituted by a footing that has an approximately rectangular plan shape and by a contiguous first head, which has a teardrop-shaped plan configuration, approximately centrally to which there is a first cavity on the bottom of which there is a first hole for engagement with said first frame.

4. The device according to claim 3, wherein said first spherical dome is provided in a first surface of said footing that during use is directed away from the knee, axially to said first spherical dome there being a second through hole.

5. The device according to claim 4, wherein in a second surface of said footing that during use is directed toward the knee there is a first recess at which there is said first substantially hemispherical seat, axially to which a third through hole is provided.

6. The device according to claim 2, wherein said first frame is approximately shaped like an inverted letter U, so as to form a base that can be positioned so as to cover the front region and part of the lateral regions of the thigh, and from which two first wings protrude which can be positioned with their free ends proximate to the two sides of the knee, wherein said first base can be associated with one of said first wings by arranging it in a complementarily shaped second seat, which is formed at one end of said first wings and on the bottom of which there is, at said first hole of said first head, a fourth hole, said first base being fixable in said second seat by means of a first screw.

7. The device according to claim 6, wherein said second base has an approximately L-shaped plan configuration so as to form a first branch and a second branch, which are approximately mutually perpendicular, a fifth through hole for engagement with said second frame being provided approximately centrally to said first branch.

8. The device according to claim 7, wherein said second spherical dome protrudes from a third surface of said second base that during use is directed toward the knee, at said second arm, a sixth through hole being provided axially to said second spherical dome.

9. The device according to claim 8, wherein said substantially flat resting abutment is formed on said third surface of said second base at said first branch and a seventh through hole is formed therein.

10. The device according to claim 7, wherein said second frame is approximately Y-shaped so as to form an approximately vertical portion that can be arranged so as to cover partially the front region of the tibia and from which two second wings protrude which can be arranged, with their free ends, proximate to the two sides of the knee, said second base being associable with one of said second wings of said second frame by arranging it in a complementarily shaped third seat formed at one end of said second wings and on the bottom of which there is, at said fifth hole of said second base, an eighth hole, said second base being fixable in said third seat by means of a second screw that is associated with said fifth and eighth holes.

11. The device according to claim 8, wherein said first arm has a substantially rectangular plan shape and has a curved central portion that during use is arranged so that its concave surface is directed toward said knee, said first arm having a first end and a second end which are substantially flat and approximately parallel to each other.

12. The device according to claim 11, wherein a fourth seat is provided at said first end of said first arm in the surface thereof that during use is directed toward the knee, and is shaped substantially complementarily with respect to said first spherical dome of said first base, axially to which a ninth hole is provided.

13. The device according to claim 12, wherein said first end of said first arm can be associated rotatably with said first base by arranging said first spherical dome in said fourth seat and by coupling these last preferably by means of an appropriately provided first rivet, inserted in said second and ninth holes, optionally with the interposition of appropriately provided first washers, said first rivet having a first stem whose diameter is smaller than the diameter of said second and ninth holes, so as to allow said first spherical dome to move in the three directions within said third seat.

14. The device according to claim 12, wherein a fifth seat is provided at said second end of said first arm, in the surface thereof that during use is directed away from the knee, and is substantially shaped complementarily with respect to said second spherical dome of said second base, axially to which a tenth hole is provided.

15. The device according to claim 14, wherein said second end of said first arm can be associated rotatably with said second base by arranging said second spherical dome in said fifth seat and by coupling them preferably by means of an appropriately provided second rivet that is inserted in said sixth and tenth holes, optionally with the interposition of appropriately provided second washers, said second rivet having a second stem whose diameter is smaller than the diameter of said sixth and tenth holes, so as to allow said second spherical dome to move in the three directions within said fifth seat.

16. The device according to claim 1, wherein said second arm has an approximately L-shaped plan configuration, so as to form a third branch and a fourth branch that are approximately mutually perpendicular.

17. The device according to claim 16, wherein said third branch is provided centrally with an increased width or expansion.

18. The device according to claim 17, wherein proximate to the free end of said third branch, in the surface thereof that during use is directed away from the knee, there is a third spherical dome, which is shaped substantially complementarily to said first seat of said first base and axially to which an eleventh hole is provided.

19. The device according to claim 18, wherein said third branch of said second arm can be associated rotatably with said first base, arranging said third spherical dome in said first seat of said first base and coupling the latter and said second arm preferably by means of a third rivet, which is inserted in said third and eleventh holes, optionally with the interposition of appropriately provided third washers, said third rivet having a third stem whose diameter is smaller than the diameter of said third and eleventh holes, so as to allow said third spherical dome to move in the three directions within said first seat.

20. The device according to claim 19, wherein proximate to the free end of said fourth branch, the surface thereof that during use is directed in the opposite direction with respect to the knee is substantially flat and has a twelfth hole.

21. The device according to claim 20, wherein said second branch of said second arm can be associated rotatably with said second arm, arranging said free flat end thereof in engagement with said complementarily shaped resting abutment of said second base, and rotatably coupling the latter and said second arm preferably by means of a fourth rivet, which is inserted in said seventh and twelfth holes, optionally with the interposition of fourth washers, the play between the fourth stem of said fourth rivet and said seventh and twelfth holes being reduced, so that said second arm can rotate with said second base only by lying on a plane that is substantially parallel to said resting abutment.

22. The device according to claim 1, further comprising means for front protection of the knee.

23. The device according to claim 22, wherein said means for front protection of the knee comprise a shell made of rigid material that is associated with said first and second frames by means of at least two bands that are fixed thereto and to two plates, each of which is rotatably associated with one of said first wings and with one of said second wings, by way of the insertion of said first and second screws, prior to their insertion in said fourth and eighth holes, in two appropriately provided slots formed in said plates.

24. The device according to claim 1, further comprising stroke limiting and shock-absorbing means.

25. The device according to claim 24, wherein said stroke limiting and shock-absorbing means comprise a second cavity, which has a polygonal and preferably approximately rectangular cross-section and is formed at the free end of said first or second wings, in such a position as to face, in the condition of maximum extension of the leg, a stop abutment provided at the free end respectively of said second or first wings.

26. The device according to claim 25, wherein a third screw is at least partially accommodated within said second cavity and comprises a fifth threaded stem and a second substantially cylindrical head which during use engages the bottom of said second cavity, a preferably cylindrical pivot protruding from said second head on the opposite side with respect to said fifth stem and being inserted during use in a first through opening that is formed in the bottom of said second cavity and being rotatably coupled therein preferably by means of a stop ring inserted in said first opening through a second lateral opening and fixed to an annular slot formed in the lateral surface of said pivot, at the free end of said pivot there being means adapted to allow to impart an axial rotation thereto.

27. The device according to claim 26, wherein said fifth stem of said third screw is screwed into a complementarily threaded third cavity that is formed axially with respect to a block, made of elastically deformable material, which in plan view is shaped substantially complementarily with respect to said second cavity and is partially inserted therein and protrudes from it with its free end, which abuts, during the mutual rotation of said first and second frames, against said stop abutment.

28. A hinge particularly for a protective device for a joint, particularly for a knee, constituted by a first base and a second base, which are rotatably connected to each other by means of a first arm and a second arm, wherein said first and second arms are arranged so as to cross each other, the ends of said first arm being both rotatably associated with said first and second bases by means of substantially hemispherical mutual engagement surfaces, one end of said second arm being rotatably associated with said first base by means of a substantially hemispherical mutual engagement surface, the other end of said second arm being associated with said second base by means of a substantially flat mutual engagement surface.

* * * * *